(12) United States Patent
Kivitz (10) Patent No.: US 11,324,480 B1
(45) Date of Patent: May 10, 2022

(54) ULTRASOUND SONOGRAPHIC IMAGING SYSTEM AND METHOD

(71) Applicant: Philip B. Kivitz, Carson City, NV (US)

(72) Inventor: Philip B. Kivitz, Carson City, NV (US)

(73) Assignee: FOCUSWEST HEALTH INC., San Rafael, CA (US)

(*) Notice: Subject to any disclaimer, the term of this patent is extended or adjusted under 35 U.S.C. 154(b) by 0 days.

(21) Appl. No.: 17/221,466

(22) Filed: Apr. 2, 2021

Related U.S. Application Data (63) Continuation of application No. 17/089,263, filed on Nov. 4, 2020, now Pat. No. 11,013,492.

(51) Int. Cl.
*A61B 8/00* (2006.01)
*A61B 8/08* (2006.01)
*A61B 8/12* (2006.01)

(52) U.S. Cl.
CPC .......... *A61B 8/4218* (2013.01); *A61B 8/0825* (2013.01); *A61B 8/0841* (2013.01); *A61B 8/12* (2013.01); *A61B 8/406* (2013.01); *A61B 8/4494* (2013.01); *A61B 8/5207* (2013.01)

(58) Field of Classification Search
CPC ....... A61B 8/4209; A61B 8/40; A61B 8/0825; A61B 5/708; A61B 8/4218; A61B 8/12; A61B 8/0841; A61B 8/4494; A61B 8/5207; G01S 15/8909
See application file for complete search history.

(56) References Cited

U.S. PATENT DOCUMENTS

| | | | |
|---|---|---|---|
| 3,765,403 A | 10/1973 | Brenden | |
| 4,233,988 A | 11/1980 | Dick et al. | |
| 4,346,867 A * | 8/1982 | Dick ................... | A61B 8/0825 248/424 |
| 4,509,368 A | 4/1985 | Whiting et al. | |
| 5,776,062 A | 7/1998 | Nields | |
| 6,459,925 B1 | 10/2002 | Nields et al. | |
| 7,264,592 B2 | 9/2007 | Shehada | |
| 10,641,893 B2 | 5/2020 | Pandey | |

(Continued)

OTHER PUBLICATIONS

M. Z. Mahmoud, M. Aslam, M. Alsaadi, M. A. Fagiri and B. Alonazi, "Evolution of robot-assisted ultrasound-guided breast biopsy systems", J. Rad. Res. Appl. Sci., vol. 11, No. 1, pp. 89-97 (Year: 2018).*

(Continued)

*Primary Examiner* — Jonathan Cwern
*Assistant Examiner* — Amal Aly Farag
(74) *Attorney, Agent, or Firm* — Weitzman Law Offices, LLC (57) ABSTRACT

A sonographic imaging device involves an at least one movable panel, coupled to an upper surface, wherein movement of the panel will alter the overall size of the opening, a tub positioned beneath the opening and defining a volume such that a body part of a human subject can freely protrude through the opening into the volume defined by the tub, at least one robotic arm having a terminal end, wherein the terminal end is position-able to multiple locations within the volume defined by the tub, and at least one high frequency ultrasound transducer located near the terminal end. A related method of acquiring sonographic images of tissue of a human subject is also described.

21 Claims, 8 Drawing Sheets

(56) References Cited

U.S. PATENT DOCUMENTS

| | | | | |
|---|---|---|---|---|
| 2003/0007598 | A1* | 1/2003 | Wang | A61B 8/5238 378/37 |
| 2005/0143638 | A1* | 6/2005 | Johnson | A61B 5/415 600/407 |
| 2006/0009696 | A1 | 1/2006 | Hanover et al. | |
| 2007/0021738 | A1* | 1/2007 | Hasser | G16H 20/40 606/1 |
| 2007/0033735 | A1 | 2/2007 | Formenti | |
| 2011/0077523 | A1* | 3/2011 | Angott | A61B 5/107 600/448 |
| 2013/0096413 | A1 | 4/2013 | Ashkenazi et al. | |
| 2013/0172753 | A1 | 7/2013 | Angott | |
| 2014/0275942 | A1 | 9/2014 | Johnson et al. | |
| 2015/0056591 | A1* | 2/2015 | Tepper | G09B 23/286 434/262 |
| 2015/0182191 | A1* | 7/2015 | Caluser | A61B 8/5246 600/440 |
| 2017/0028218 | A1* | 2/2017 | De Neve | A61B 6/0435 |
| 2017/0120078 | A1* | 5/2017 | Payne | A61B 5/055 |
| 2017/0215841 | A1 | 8/2017 | Pandey et al. | |

OTHER PUBLICATIONS

Wells et al., "An Immersion Scanner For Two-Dimensional Ultrasonic Examination Of The Human Breast" Ultrasonics pp. 220-228 (Oct. 1968).

Dick et al., "A New Automated, High Resolution Ultrasound Breast Scanner" Ultrasonic Imaging, vol. 1, pp. 368-377 (1979).

Maturo et al., "Ultrasound of the Whole Breast Utilizing a Dedicated Automated Breast Scanner" Radiology vol. 137 pp. 457-463 (1980).

Arditi et al., "An Annular Array System for High Resolution Breast Echograpy" Ultrasonic Imaging vol. 4, pp. 1-31 (1982).

Cole-Beuglet et al., "Clinical Experience with a Prototype Real-Time Dedicated Breast Scanner" American Journal of Radiology, vol. 139, pp. 905-911 (1982).

Leach et al., "Comparison Of Ultrasound Tomography Methods In Circular Geometry" Medical Imaging 2002 Ultrasonic Imaging and Signal Processing, Michael F. Insana, William F. Walker, (Eds.), Proceedings of SPIE vol. 4687, pp. 362-377 (2002).

Cannata et al., "Design of Efficient, Broadband Single-Element (20-80 MHz) Ultrasonic Transducers for Medical Imaging Applications" IEEE Transactions on Ultrasonics, Ferroelectrics, and Frequency Control, vol. 50, No. 11, pp. 1548-1557 (2003).

Dempsey, P., "The History of Breast Ultrasound" J. Ultrasound Med., vol. 23, pp. 887-894 (2004).

Duric et al., "Multi-modal breast imaging with ultrasound tomography" Medical Imaging 2008: Ultrasonic Imaging and Signal Processing, Stephen A. McAleavey, Jan D'hooge (Eds.), Proc. of SPIE vol. 6920, p. 69200O-1 thru -8 (2008).

Kelly et al., "Breast cancer detection using automated whole breast ultrasound and mammography in radiographically dense breasts" Eur Radiol vol. 20, pp. 734-742 (2010) [DOI 10.1007/s00330-009-1588-y].

Andre et al., "Quantitative Volumetric Breast Imaging with 3D Inverse Scatter Computed Tomography" Proceedings of the 34th Annual International Conference of the IEEE EMBS, San Diego, California USA, Aug. 28-Sep. 1, 2012, pp. 1110-1113 (2012).

Wiskin et al., "Non-Linear Inverse Scattering: High Resolution Quantitative Breast Tissue Tomography" J. Acoust. Soc. Am. 131 (5), pp. 3802-3813 (2012).

Andre et al., "Clinical Results with Ultrasound Computed Tomography of the Breast" Quantitative Ultrasound in Soft Tissues, pp. 395-432 (2013).

Wiskin et al., "Three-Dimensional Nonlinear Inverse Scattering: Quantitative Transmission Algorithms, Refraction Corrected Reflection, Scanner Design And Clinical Results" Proc. Mtgs. Acoust. 19, 075001 (2013) [doi 10.1121/1.4800267].

Kaplan, S., "Automated Whole Breast Ultrasound" Radiol. Clin. N. Am, vol. 52, pp. 539-546 (2014).

Sheaff, C. "All-Optical Ultrasound Transducers for High Resolution Imaging", PhD Thesis Univ. of MN (2014).

Lenox et al., "Imaging Performance of Quantitative Transmission Ultrasound" International Journal of Biomedical Imaging vol. 2015, Article ID 454028, 8 pages [http://dx.doi.org/10.1155/2015/454028].

Malik et al., "Objective Breast Tissue Image Classification Using Quantitative Transmission Ultrasound Tomography" Sci. Rep. 6, 38857; doi: 10.1038/srep38857 (2016).

Iuanow et al., "Accuracy of Cyst Versus Solid Diagnosis in the Breast Using Quantitative Transmission (QT) Ultrasound" Acad Radiol. vol. 24(9), pp. 1148-1153 (2017).

Farrokh et al.;., "SOFIA: A Novel Automated Breast Ultrasound System Used on Patients in the Prone Position: A Pilot Study on Lesion Detection in Comparison to Handheld Grayscale Ultrasound" Geburtsh Frauenheilk, vol. 78, pp. 499-505 (2018).

Zeist et al., "Automated Three-dimensional Breast US for Screening: Technique, Artifacts, and Lesion Characterization" RadioGraphics vol. 38(3) pp. 663-683 (2018) [https://doi.org/10.1148/rg.2018170162].

Malik et al., "Breast Cyst Fluid Analysis Correlations with Speed of Sound Using Transmission Ultrasound" Acad Radiol. vol. 26(1), pp. 76-85 (2019).

Ali et al. "Imaging Properties Of 3D Printed Breast Phantoms For Lesion Localization And Core Needle Biopsy Training" 3D Printing in Medicine vol. 6, No. 4 (2020) [doi.org/10.1186/s41205-020-00058-5].

Nicosia et al., "Automatic Breast Ultrasound: State Of The Art And Future Perspectives" ecancer vol. 14, No. 1062 (2020) [https://doi.org/10.3332/ecancer.2020.1062].

Sak et al., "Whole Breast Sound Speed Measurement from US Tomography Correlates Strongly with Volumetric Breast Density from Mammography" Journal of Breast Imaging, vol. XX, Issue XX, pp. 1-9 (2020)[doi:10.1093/jbi/wbaa052].

Alandoli, E. et al., A Critical Review of Control Techniques for Flexible and Rigid Link Manipulators, Robotica, vol. 38, No. 12p. 2239-2265 (2020).

Burgner-Kahrs, J., et al.. Continuum Robots for Medical Applications: A Survey, IEEE Transactions on Robotics, vol. 31, No. 6, pp. 1261-1280 (2015).

Chirikjian G.S., et al., A Modal Approach to Hyper-Redundant Manipulator Kinematics, IEEE Transactions on Robotics and Automation, vol. 10, No. 3, pp. 343-354 (1994).

Craig, J.J., Introduction to Robotics: Mechanics and Control (3d Ed ), Pearson Prentice Hall, Upper Saddle River, NJ (2005) at Ch. 1, Section 1.2 pp. 4-5.

Lathlean J., et al., Infrared thermography in marine ecology: methods, previous applications and future challenges. Mar. Ecol. Prog Ser, vol. 514, pp. 263-277 (2014).

McCafferty, D.J., et al., Estimating metabolic heat loss in birds and mammals by combining infrared thermography with biophysical modelling, Comp. Biochem. Physiol., Part A, vol. 158(3), pp. 337-345 (2011).

Sarawade, A.A., et al., Infrared Thermography and its Applications: A Review, Proceedings of the 3rd International Conference on Communication and Electronics Systems (ICCES), pp. 280-285 (2018).

Tattersall, G.J., Infrared thermography: A non-invasive window into thermal physiology, Comparative Biochemistry and Physiology Part A, vol. 202, pp. 78-98 (2016).

Vall, M.O.M.. Modeling and Networked Control of Two-rigid link Robot Arm, WSEAS Transaction on Systems and Control, vol. 15, pp. 375-382 (2020).

* cited by examiner

FIG. 9

ULTRASOUND SONOGRAPHIC IMAGING SYSTEM AND METHOD

FIELD OF THE INVENTION

This disclosure relates generally to imaging devices and, more particularly, to medical imaging systems involving ultrasound.

BACKGROUND

Medical imaging systems are important tools in the diagnosis of medical conditions. However, in many cases ultrasound sonography is not usually employed for screening for various reasons including the skill required to perform the imaging, the requirement that a radiologist review a large number of images, the training and skill required to account for tissue distortions introduced by the constraining apparatus of the imaging system, and cost. This is particularly true for sonography as used for breast cancer screening.

Thus, there remains a need for a medical imaging system that can positively address at least some of these issues and thereby improve an important medical diagnostic tool.

SUMMARY

One aspect of this disclosure involves a sonographic imaging device having an imaging unit including an upper surface having an opening therein; at least one movable panel, coupled to the upper surface, wherein sliding movement of the panel in a plane parallel to the upper surface will alter the overall size of the opening; a tub positioned beneath the opening and defining a volume for holding fluid such that, in use, a breast of a human subject can freely protrude through the opening into the fluid within the volume defined by the tub; at least two independently controllable robotic arms, each having a terminal end and more than 3 degrees of freedom, wherein the terminal end of each is position-able to any of multiple angles at multiple locations within the volume defined by the tub to allow for imaging of the human subject's axillary lymph nodes associated with the breast as well as the breast; and at least one high frequency ultrasound transducer located near the terminal end of the at least two independently controllable robotic arms.

Another aspect of this disclosure involves a method of acquiring sonographic images of unconstrained breast tissue of a human subject positioned on a surface of an imaging unit, when the breast's internal tissue is present within fluid within a volume of a tub. The method involves i) adjusting a size of an opening, defined by the surface of the imaging unit, by sliding a movable panel in a plane parallel to the surface in order to accommodate a portion of the human subject containing the internal breast tissue and allow for imaging of the axillary lymph nodes associated with the human subject's breast; ii) conducting a low frequency scan of the internal breast tissue, from a vantage point at a first position within the tub, using a low frequency ultrasound transducer array unit present within the fluid within the tub; iii) identifying specific tissue of the internal tissue that is to be subjected to local high frequency ultrasound imaging; iv) concurrently maneuvering within the fluid within the volume, in a combination of X, Y and Z directions, a distal terminal end of at least one robotic arm of at least two independently controllable robotic arms, each independently having more than 3 degrees of freedom, the at least one robotic arm having a high frequency transceiver near the distal terminal end thereof, within the tub to a new position that is closer to the specific tissue and suitable for conducting local high frequency ultrasound imaging of the specific tissue from a first vantage point different from the vantage point of the low frequency ultrasound transducer array unit; v) obtaining sonographic data, using the high frequency transceiver, from which at least one image of the specific tissue from the vantage point can be generated; and vi) storing the sonographic data resulting from at least the high frequency imaging in non-transitory storage.

BRIEF DESCRIPTION OF THE DRAWINGS

This disclosure is further described in the detailed description that follows, with reference to the drawings, in which.

DETAILED DESCRIPTION

Device Structures

Figure 1:
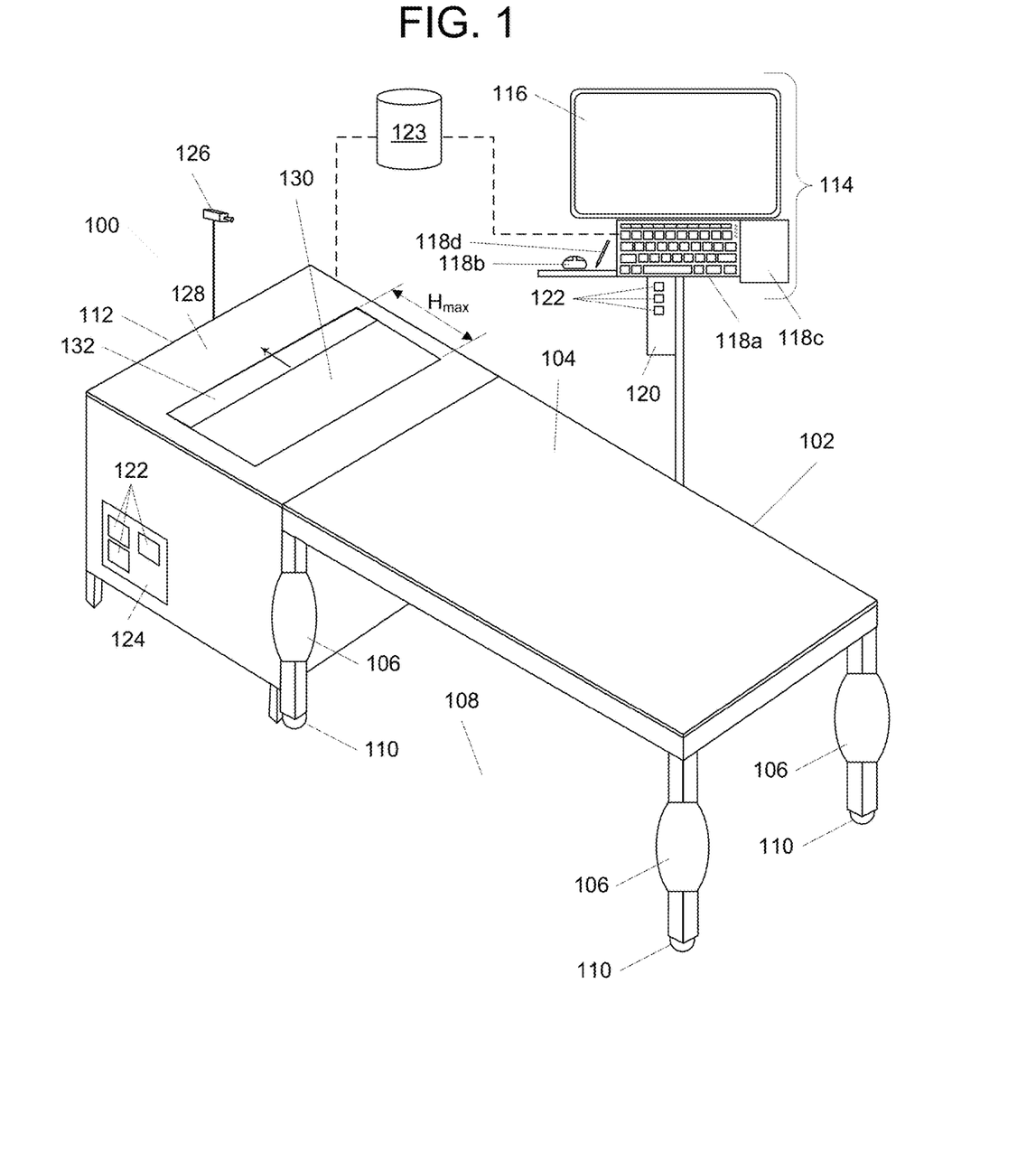
FIG. 1 illustrates, in simplified form, an external perspective view of an example implementation (not to scale) of ultrasound sonographic imaging system for imaging of human tissue according to the teachings herein.

FIG. 1 illustrates, in simplified form, an external perspective view of an example implementation (not to scale) of ultrasound sonographic imaging system ("USIS") 100 for imaging of human tissue (sometimes also referred to as "ultrasound computer tomography" or simply "ultrasound") according to the teachings herein. The USIS 100 includes a supporting table 102 that is intended for a human subject to lie on it, in a prone or substantially prone position. Depending upon the particular implementation, the upper surface 104 of the supporting table may be flat or contoured and will typically include some form of padding (e.g., foam or memory foam) to improve the comfort of the human subject during imaging.

Depending upon the particular implementation, the supporting table 102 may optionally include electromechanical and/or hydraulic mechanisms 106 therein, such as gears, servos, push rods, etc. to allow the supporting table 102 to be raised or lowered relative to the ground 108 to thereby assist the human subject in getting on or off. In addition, in some implementations the mechanisms 106 can optionally be constructed so that the used to tilt the upper surface 104 relative to a horizontal plane.

Additionally, or alternatively, the supporting table 102 may include wheels 110 that will allow it to be repositioned or moved.

The USIS 100 further includes an imaging unit 112 which, depending upon the particular implementation be part of, or may be rigidly attached to, the supporting table 102, or it may be a physically separate unit which, in use will abut, or be in close proximity to, the supporting table, such as shown in FIG. 1. In some implementations where the imaging unit 112 is a physically separate unit, the supporting table 102 can simply be a conventional gurney or examining table.

The USIS 100 further includes an operator console 114, made up of, for example, a display screen or monitor 116 and at least one input device, for example, a keyboard 118a, mouse 118b, touch pad 118c, stylus 118d, or in some cases, the input device 118 can be part of the monitor 116 if the monitor is a "touch screen"-type monitor. The operator console 114 may be located near the imaging unit 112 or may be remote from it. The operator console 114 is coupled to the imaging unit 112 either by a wired (e.g., ethernet, coaxial cable, fiber optic cable, twisted pair) or a short range wireless (e.g., WiFi, Bluetooth®, LTE-A, LTE-M, NB-IoT, Sigfox, WiMAX, Wi-Sun, Z-Wave, etc.) connection to enable a technician to control aspects of the imaging unit's 112 operation as will be described herein. In certain implementations, the operator console 114 may also be connected, directly or indirectly, to the supporting table 102 to control its operation, for example, the mechanisms 106, if such functionality is present.

The operator console 114 may itself include a computer 120 having one or more processors 122, or it may act as a terminal for one or more computers 124, each having one or more processors 122, that is located in, or associated with, the imaging unit 112. Depending upon the particular implementation, a processor 122 may have a single core or multiple cores. Additionally, non-transitory storage 123 may be coupled to the operator console 114 and/or imaging unit 112 for purposes of storing files containing data obtained as part of, or resulting from, the imaging process. Optionally, and particularly where the operator console 114 is remote from the imaging unit 112, the USIS 102 may also include one or more cameras 126 that will, for example, allow a technician located near the operator console 114 to view a human subject positioned on top of the supporting table 102, and potentially images from one or more a perspectives within the imaging unit's 112 interior, as will be described in greater detail below.

The upper surface 128 of the imaging unit 112 (which may also be contoured and/or padded for the comfort of the human subject being imaged) includes an opening 130 whose extent can be varied through movement of one or more sliding panel(s) 132 between a "height" of typically Hmax or less in order to facilitate imaging of the axillary lymph nodes (also sometimes referred to as "axilla") by virtue of ensuring the opening size encompasses a height of the subject being imaged from about the collarbone to just below the inframamary fold (also sometimes referred to as the inframammary crease). Typically, Hmax will be about 38 cm (15") (i.e., covering humans falling within 99.9% or more in anthropometric scale), but that value could be larger or smaller for particular populations.

FIGS. 2A-2D illustrate, in simplified form, part of a top down view (not to scale) of two different representative example implementations of the upper surface 128 of example imaging units 112a, 112b similar to the imaging unit 112 of FIG. 1.

Figure 2A:
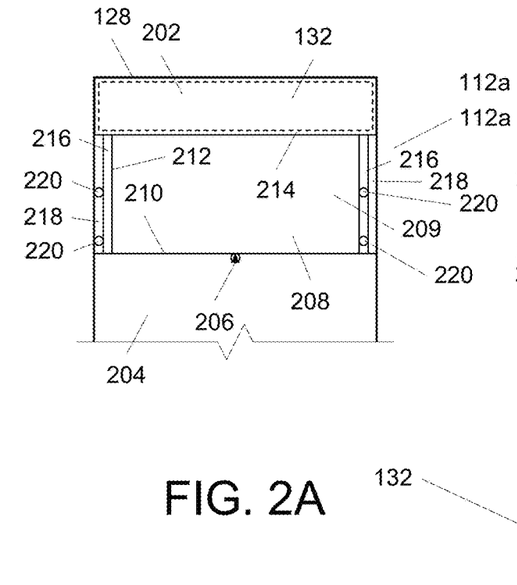
FIGS. 2A-2D illustrate, in simplified form, part of a top down view (not to scale) of two different representative example implementations of the upper surface of example imaging units similar to the imaging unit of FIG. 1.
Figure 2B:
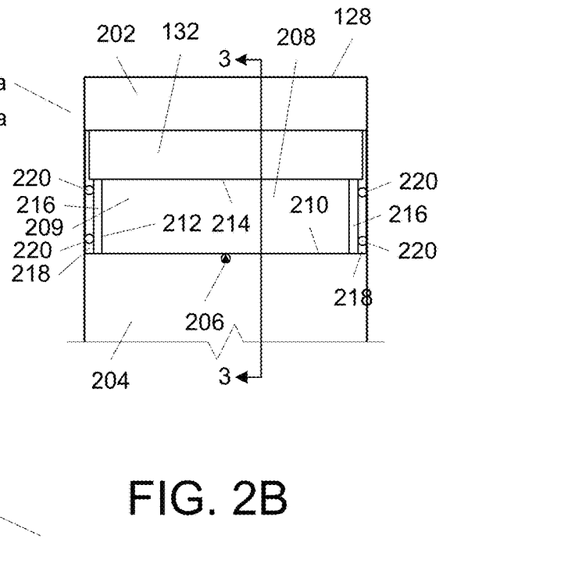

FIGS. 2A-2B illustrate, in simplified form, part of a top down view of a first example upper surface 128 of an imaging unit 112a. As shown, the upper surface 128 has a head portion 202 and a waist portion 204, the terms "head" and "waist" merely denoting (for purposes of explanation) those portions which will be closer to that corresponding part of a human subject during imaging.

The waist portion 204 includes a registration indicator 206 with which a human subject will be aligned, as described below, for purposes of imaging. The imaging unit 112 further includes a tub 208, which can be filled with a fluid, that will typically be maintained during imaging to roughly 30° C. to 38° C. (i.e., within about 5° C. to 10° C. of normal body temperature) for the comfort of the human subject being imaged and to prevent tissue distortion. The fluid is a liquid conducive to transmission of ultrasonic waves for imaging, such as de-aerated water, or other suitable fluids known in the sonography field.

The tub 208 is accessible via an variable sized opening 209 that is defined by the upper edge 210 of the waist portion, the sidewalls 212 of the tub 208 and the position of the lower edge 214 of the sliding panel 132 of the head portion 202. As shown in FIG. 2A, the sliding panel 132 is in its fully recessed position, yielding an opening 209 with the height of Hmax.

As shown, a space 216 optionally exists between the sidewalls 212 of the tub 208 and the sidewalls 218 of the imaging unit 112a to allow for overflow/displacement of fluid from the tub 208. Finally, as shown in FIGS. 2A-2B, the upper surface 128 of the imaging unit 112 may optionally also include one or more mounting locations 220 to which a movable robot arm (not shown but as will be described in greater detail below) may optionally be mounted.

FIG. 2B illustrates, in simplified form, the imaging unit 112a of FIG. 2A but the sliding panel 132 of the head portion 202 has been fully slid or extended towards the waist portion 204, thereby reducing the size of the opening 209.

Figure 2C:
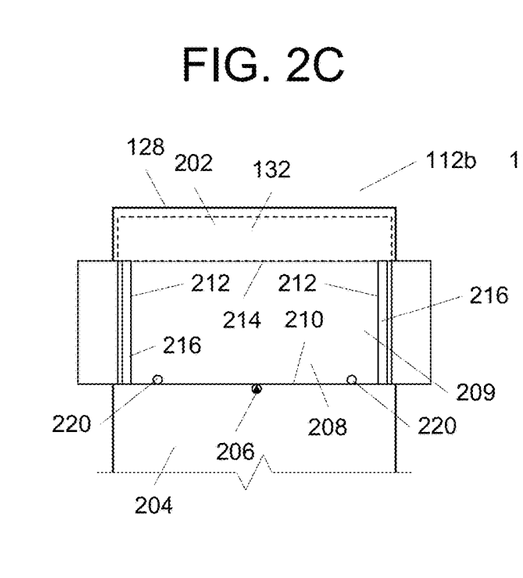
Figure 2D:
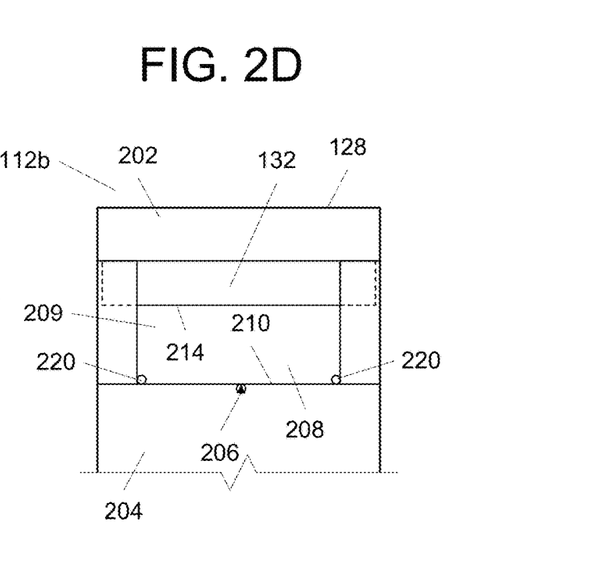

FIGS. 2C-2D illustrate, in simplified form, part of a top down view of a second example upper surface 128 of an imaging unit 112b that is similar to that of FIGS. 2A-2B except that the imaging unit 112b includes at least one, and as shown two, side panels 222 that can be moved to further reduce the size of the opening 209. As shown in FIG. 2C, the side panels 222 and sliding panel 128 are fully retracted and, in FIG. 2D, the side panels 222 and sliding panel 128 are fully extended.

Although the variable size opening 209 in each of FIGS. 2A-2D are generally rectangular, alternative implementations may incorporate variable openings which, when fully opened are any closed geometric shape, provided it is sized to allow for, at its largest, imaging of 99+% of all human subjects based upon anthropometric data, to thereby provide, in this specific application, access to the entire breast area as well as the associated axillary lymph nodes (i.e., an area typically extending from about the clavicle to just below the inframammary fold in one direction and ideally from about the outer deltoid/tricep muscle to the sternum in the other. Depending upon the particular implementation, the sliding panels that can be moved to adjust the size of the opening need not have straight sides, rather, they can alternatively be curved or, in the case of openings that are circular or oval, the size of the opening could be adjusted using an iris-like sliding panel, the key being, in the case of breast imaging applications, the opening can allow for imaging of both a breast and associated axillary lymph nodes without repositioning of the human subject.

Figure 3:
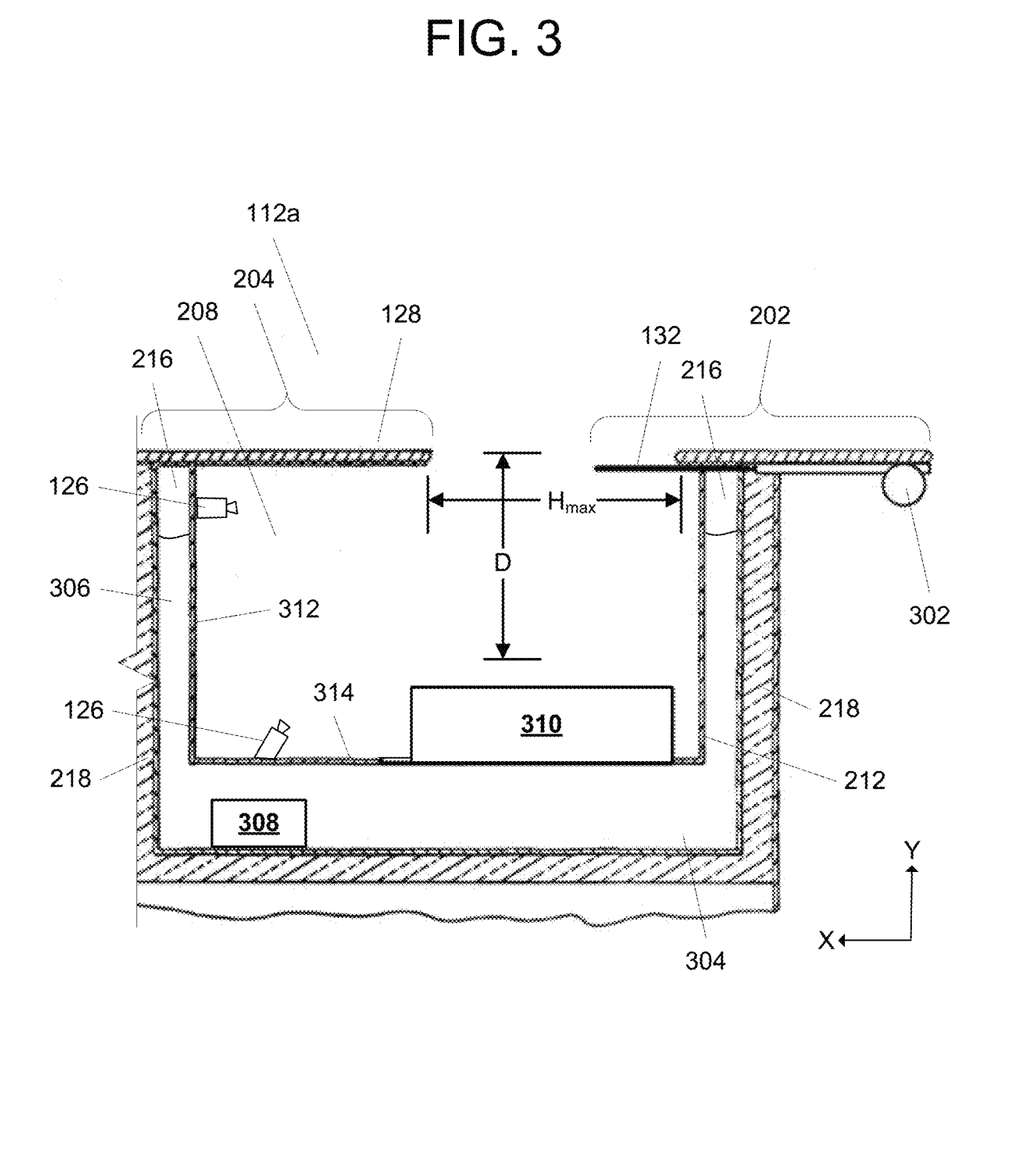
FIG. 3 illustrates, in simplified form, a cross sectional view of the imaging unit of FIG. 2B.

FIG. 3 illustrates, in simplified form, a cross sectional view of the imaging unit 112a of FIG. 2B taken at 3-3. As can be seen in FIG. 3, the sliding panel 132, which is partially extended, is optionally coupled to a device 302, for example, an electric motor, electromechanical actuator or solenoid, that can (under control of one of the processors 124) move the sliding panel 132 through its range of motion, and thereby change the height of the opening 209.

As shown, the example imaging unit 112a further includes an overflow/reservoir chamber 304 which contains the fluid 306 that is used in the tub 208. It is to be understood however, that having such an overflow/reservoir chamber 304 as part of the imaging unit 112a is optional, in that the fluid 306 can be sourced from a reservoir that is not part of the imaging unit 112a in some implementations and inflow can be controlled so that final filling of fluid 306 occurs once the subject is situated and the freely hanging breast is in the desired position within the tub 208. In addition, for simplicity, the piping or tubing through which the fluid can enter/leave the tub is not shown, but should be understood to be present.

For implementations that include a reservoir chamber 304 as part of the imaging unit 112a, other components 308 may also be present, for example, one or more pumps, heating elements, thermocouples or a thermostat, filtration and or sterilization elements, UV sterilization lights, etc.

In addition, the tub 208 may optionally also, or alternatively, have one or more cameras 126 located within it in order to provide a real time view from the interior of the tub 208 of the relevant areas of the human subject being imaged and/or the position of one or more robotic arms (not shown), as will be described below. The specific placement of such one or more cameras 126 is a matter of design choice, since such placement(s) can be a function of the particular implementation. By way of non-limiting example, as shown in FIG. 3, one camera 126 is coupled to a surface 312 of the side surface 212 of the tub 208 and another camera is coupled to a bottom surface 314 of the tub 208. It is to be understood that placement of the one or more cameras can be anywhere in the tub 208 that does not interfere with imaging including, additionally or alternatively, a camera can be located on a robotic arm. Depending upon the particular implementation, such robotic arm can be dedicated to the camera or it can be one of the arms having one or more transducer(s) as will be described below. In addition, optionally, the tub 208 can have associated with it, and/or one or more robotic arms can contain, one or more lighting elements (e.g., LEDs, optical fiber light tube(s), conventional light bulbs, etc.), for example, for purposes of: facilitating or assisting with: camera imaging, subject positioning or illumination, visual navigation/manipulation and/or positioning of a robotic arm.

In addition, optionally, an ultrasound transducer array unit 310 is located within and near the bottom of the tub 208, which is used, in the conventional manner, for reflective ultrasonic imaging of the breast of the human subject located within the opening 209 that extends into the tub 208 to a depth that is less than "D" indicated. By way of non-limiting example, one representative device that could serve as the ultrasound transducer array unit 310 may be a unit such as shown and described in U.S. Pat. No. 4,233,988 at FIG. 3 and in the associated description. The ultrasound transducer array unit 310 is used to image the breast of the human subject in a direction essentially perpendicular to the upper surface 128 of the imaging unit 112, in depending upon the particular implementation and unit 310 type and construction, A-mode, B-mode, in some cases C-mode, and/or some combination thereof, to obtain sonographic images in depth extending from a plane defined by the pectoral muscles to a plane defined by the nipple/areola. In general, the low frequency ultrasound transducer array unit 310 is configured to (1) emit low frequency ultrasonic waves at a frequency within the range of 1.5 MHz to 10 Mhz, and more typically a frequency between 2 MHz and 4 MHz, and most commonly at 2.5 MHz, and (2) receive reflected ultrasound waves, during the series of scans. This type of ultrasound imaging device and approach is, itself, conventional, so it need not be discussed further herein. The reflected ultrasound waves are likewise received and converted in a conventional manner into an image in certain depth increments. As contemplated herein, imaging units 112 constructed according to the teachings herein will typically be configured such that scans will be in 2 mm increments having 0.5 mm of overlap to ensure that small lesions present will be captured. However, it should be understood that the particular specified scan increment and overlap is not a requirement, but merely stated for purposes of understanding, and it is to be appreciated that other increments and overlap amounts can be used and, in some cases, may be specified via the operator console 114.

Finally, as will be discussed in connection with FIGS. 4-5 below, the tub 208 advantageously includes one or more movable robotic arms (not shown in FIG. 3) having one or more ultrasound transducers on or near the terminal end.

Figure 4:
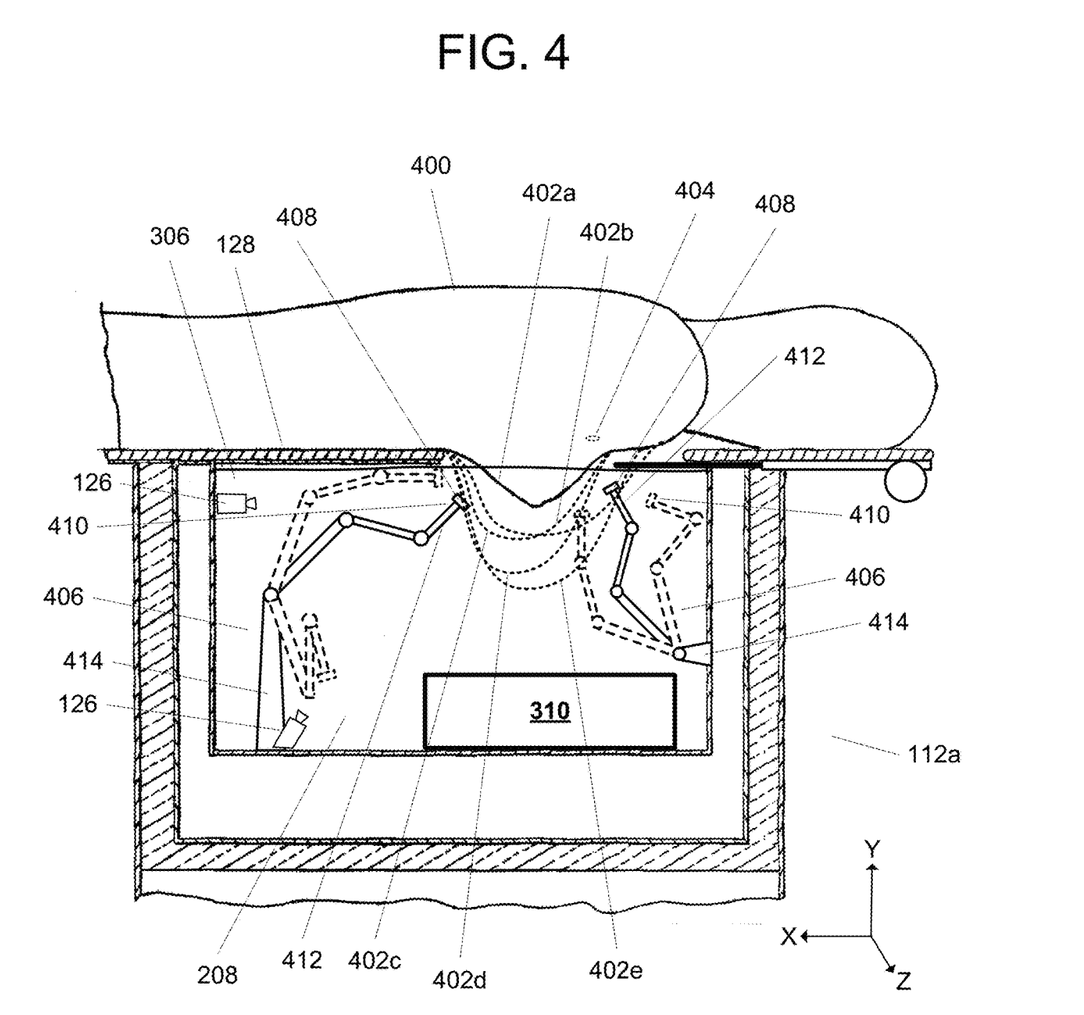
FIG. 4 illustrates, in simplified form, the cross sectional view of the imaging unit of FIG. 3, but with a representation of part of human subject(s) lying in the prone position on the upper surface of the imaging unit.

FIG. 4 illustrates, in simplified form, the cross sectional view of the imaging unit 112a of FIG. 3, but with a representation of part of human subject(s) 400, having various sized and shaped breast(s) 402a-402e, shown lying in the prone position on the upper surface 128 of the imaging unit 112a so that the breast(s) 402a-402e hangs buoyantly pendant into the fluid 306 in the tub 208 without any constraint or tethering. As can be seen in FIG. 4, by virtue of the variable opening 209, the axillary lymph nodes 404 of the human subjects 400 can be imaged along with the breasts.

As mentioned above, one or more robotic arms 406 are also present in the tub 208. A robotic arm 406 includes one or more joints that enable a transducer 408 located at or near a terminal end 410 of the robotic arm 406 to be moved in any combination of X, Y and Z directions. As shown, the robotic arms 406 comprise a series of rigid arms coupled by joints, however, wire controlled snake-type robotic arms (i.e., made up of multiple individual serially connected segments) can be used as well, or alternatively. Depending upon the particular implementation, the transducer 408 can be rigidly coupled to a subpart 412 of the robotic arm 406, or it can be coupled at or near the terminal end 410 by a connection that allows the transducer 408 to swivel independent of movement of the robotic arm 406. Note here that the transducer 408 is said to be "at or near" the terminal end 410 because the transducer 408 (which may actually be a single device or an array of 2 or more individual transducers) is a 3 dimensional component that, for some implementations, may be on the side of a subpart 412 instead of sticking off the terminal end 410. In general, the output part of the transducer should be less than 5 cm from the terminal end, and ideally, within 1 cm of the terminal end. Similarly, for some implementations, a camera 136 can be located on the robotic arm as well, in such implementations, typically at or near the terminal end.

For yet other implementations, transducer 408 can be or include one or more fiber optic ultrasound transmitters which apply photoacoustic principles to generate ultrasound through an optical fiber, for example as described in U.S. Patent Publication Nos. 2013/0096413 and 2014/0275942, the entirety of both of which are incorporated herein by reference.

The movement of a transducer 408 via the robotic arm can occur under control of an operator of the terminal 114, in an automated fashion using machine vision, or using some combination thereof, in order to orient the the transducer in the proper position and at the proper distance for the desired localized imaging.

As briefly noted above, the transducer 408 may be a single frequency devise, a multiple frequency device, or an array of single or multiple frequency devices, selected so as to emit high frequency (HF) ultrasound radiation (typically in the range of 10 MHZ to 80 MHz) in order to specifically obtain sharper, more detailed, images of the contents (typically some form of lesion, abnormal tissue or calcification) within an area of interest. Depending upon the particular implementation, with some implementations, the transducer 408 is constructed to emit at a single center frequency, whereas in other implementations, it can be a variable transducer that emits at more than one center frequency. In still other implementations, the transducer 408 can be an auxiliary transducer array made up of multiple individual transducers (e.g., arranged as a linear or phased array).

Depending upon the particular implementation the part of the robotic arm 406 opposite the terminal end 410 (for simplicity of understanding referred to herein as the "base" 414 of the robotic arm 406) can be coupled anywhere within the tub 208 volume that does not interfere with imaging, e.g., on any side surface 312 of the tub 208, the bottom surface 314 of the tub 208, or even an underside of the upper surface 128 (not shown).

Still further, and advantageously, by virtue of having a robotic arm 406 a specific area of interest can be imaged from multiple angles during the same imaging procedure with higher resolution (due to the higher frequency transducer), and, for many implementations, not only can the imaging of the area of interest be performed using reflected ultrasound radiation, but when a pair of transceivers are present on two or more separate robotic arms 406, then, advantageously, localized through-transmission ultrasound imaging can be performed as well when the pair of transceivers are positioned on opposite sides of the local area of interest, with one transceiver emitting ultrasonic radiation and ignoring reflected back ultrasound and the other transceiver, on the opposite side of the area of interest, receiving the through-transmitted ultrasound radiation.

Figure 5:
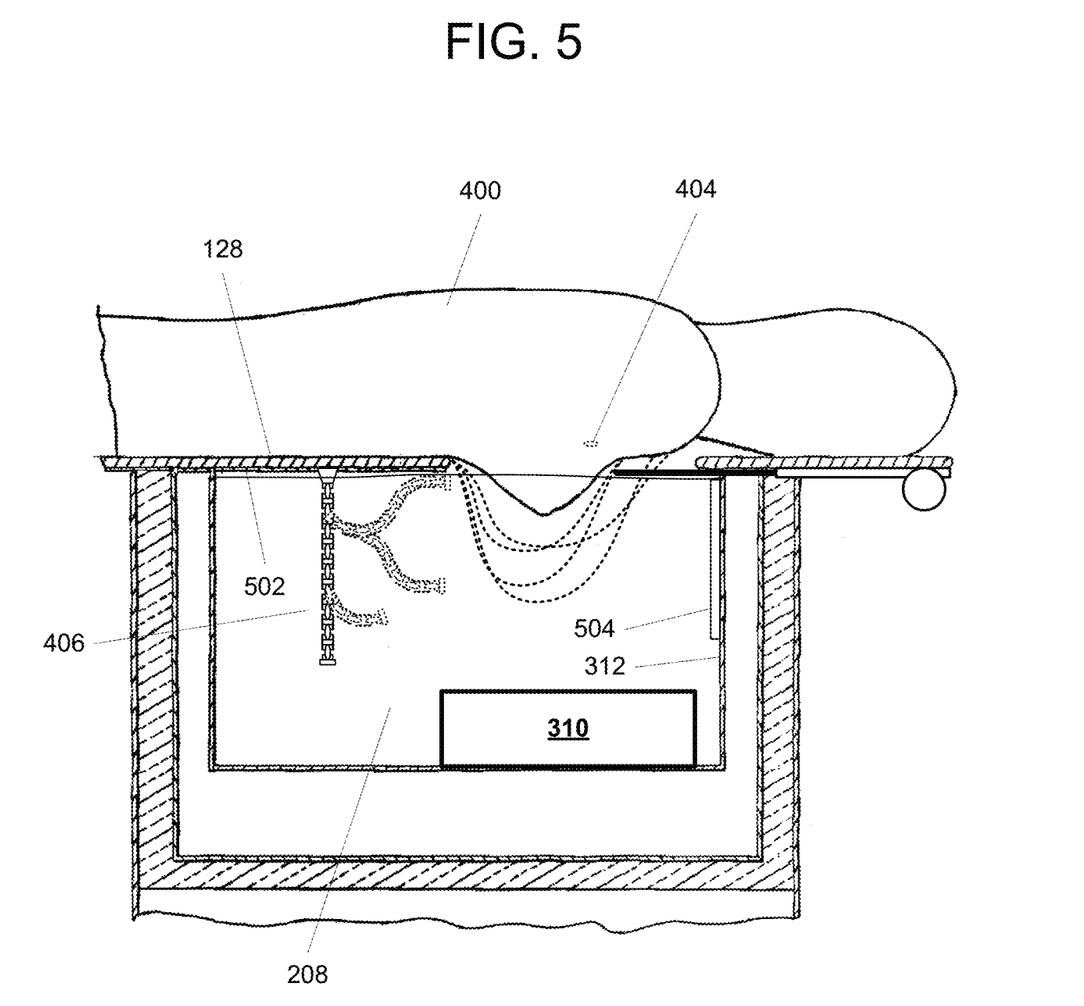
FIG. 5 illustrates, in simplified form, a cross sectional view of an example alternative imaging unit implementation that is similar to FIG. 4, except that, with this implementation, one of the potentially multiple robotic arms is coupled to an underside of the upper surface.

FIG. 5 illustrates, in simplified form, a cross sectional view of an example alternative imaging unit 112 implementation that is similar to FIG. 4, except that, with this implementation, one of the potentially multiple robotic arms 406 (only one of which is shown) is coupled to an underside 502 of the upper surface 128. In addition, at least one ultrasound receiver array 504 is within the tub and, as shown is coupled to a side surface 312 of the tub 208. With this configuration, an alternative version of through-transmission imaging can optionally or alternatively be performed.

Finally, advantageously, through use of the teachings herein, it is to be appreciated that robotic arms such as described herein can be retrofit into some existing breast ultrasound machines where that human subject being imaged lies prone above a fluid-filled tub.

Figure 6:
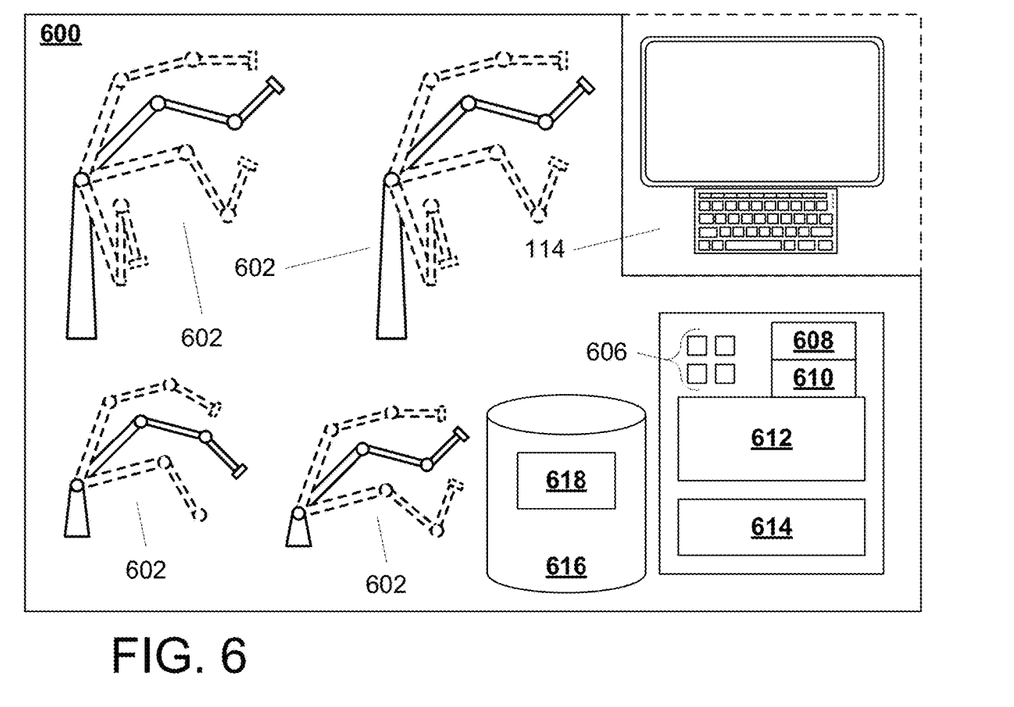
FIGS. 6-7 illustrate, in simplified form, representative examples of components for two example retrofit kits that can be used to retrofit an existing ultrasound machine to enable it to operate in accordance with the teachings herein.
Figure 7:
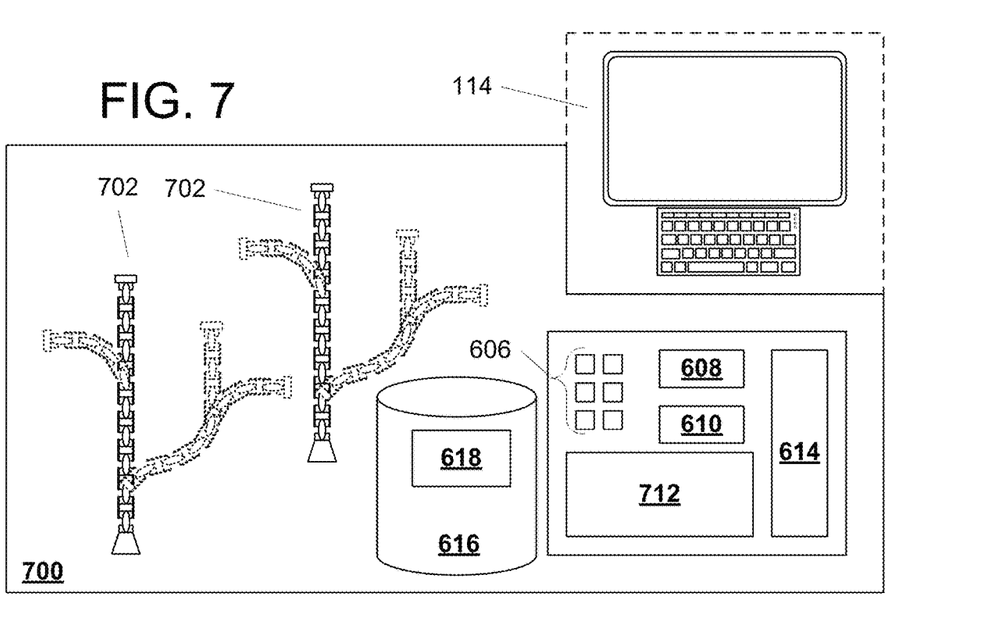

FIGS. 6-7 illustrate, in simplified form, representative examples of components for two example retrofit kits 600, 700 that can be used to retrofit an existing ultrasound machine to enable it to operate in accordance with the teachings herein. Of course, such robotic arms must be constructed such that the relevant portions that will be present in the fluid are sealed or of a type that will not be adversely affected by the fluid in the tube 208 or pose a danger (e.g., of electrical shock during use).

The retrofit kit 600 of FIG. 6 includes one or more robotic arms 602, similar to those of FIGS. 4-5 (i.e., of a type having rigid segments coupled together via movable joints), each constructed to readily physically couple to or within part of an imaging unit, for example, via a mounting location 220 such as shown in FIGS. 2A-2D, or inside a tub of the imaging unit itself. The retrofit kit 600 also includes a robotic arm control unit 604, comprising one or more processors 606, which, depending upon the particular kit, may be single core processors or multicore processors. The robotic arm control unit 604 also may include RAM 608, ROM 610. In order to control the robotic arms based upon instructions from the one or more processors 606, the robotic arm control unit 604 includes motion control circuitry that will, during operation, convert the instructions from the one or more processors 606 (which may be general purpose processors 124 as described above or special purpose processors) into electrical signals that will effect controlled movement of the installed robotic arms 602. Finally, the robotic arm control unit 604 includes communications (e.g., I/O) circuitry 614 that provides an interface (wired or wireless) to an operator control unit 114.

The retrofit kit 600 further may include auxiliary storage 616 that can be used to sore any one or more of: raw transceiver data, image data (for example, Digital Imaging and Communications in Medicine (DICOM) data) created from the raw transceiver data, proprietary and/or third-party software/programming 618 to effect the conversion of the raw transceiver data to the DICOM data, and/or for viewing, analyzing and or converting/exporting image data into other formats, for analysis, visualization and/or .STL or .OBJ files for 3D printing using, for example, OsiriX (available via www.osirix-viewer.com), InVesalius (available via www.c-ti.gov.br/pt-br/invesalius), 3DSlicer (available via www.slicer.org), etc. to name a few. Using such program(s), visualization and/or 3D printing of tissue corresponding to some or all of the image data can be performed. In this manner, for example, a 3D image of specific tissue can be reproduced for, for example, examination and/or surgical procedure planning.

The retrofit kit 700 of FIG. 7 is similar to the retrofit kit 600 of FIG. 6 except, this retrofit kit 700 includes one or more robotic arms 702 which, as shown, are snake-type robotic arms made up of multiple segments that provide a large number of degrees of freedom allowing for a wide variation in articulation, and the associated motion control circuitry 712 necessary for controlling those snake-type robotic arms 702.

Having described the structures of various representative implementation examples, examples of generic processes by which such example implementations are used will now be described.

Imaging Process

In general, it is intended that both the breast tissue and associated axilla will be imaged during the same procedure, although this is not a requirement. The human subject will also have removed clothing covering at least the portion of their torso extending from the collar bone on the side(s) to be imaged down to several centimeters below the inframammary fold and from the sternum to the shoulder joint.

Figure 8:
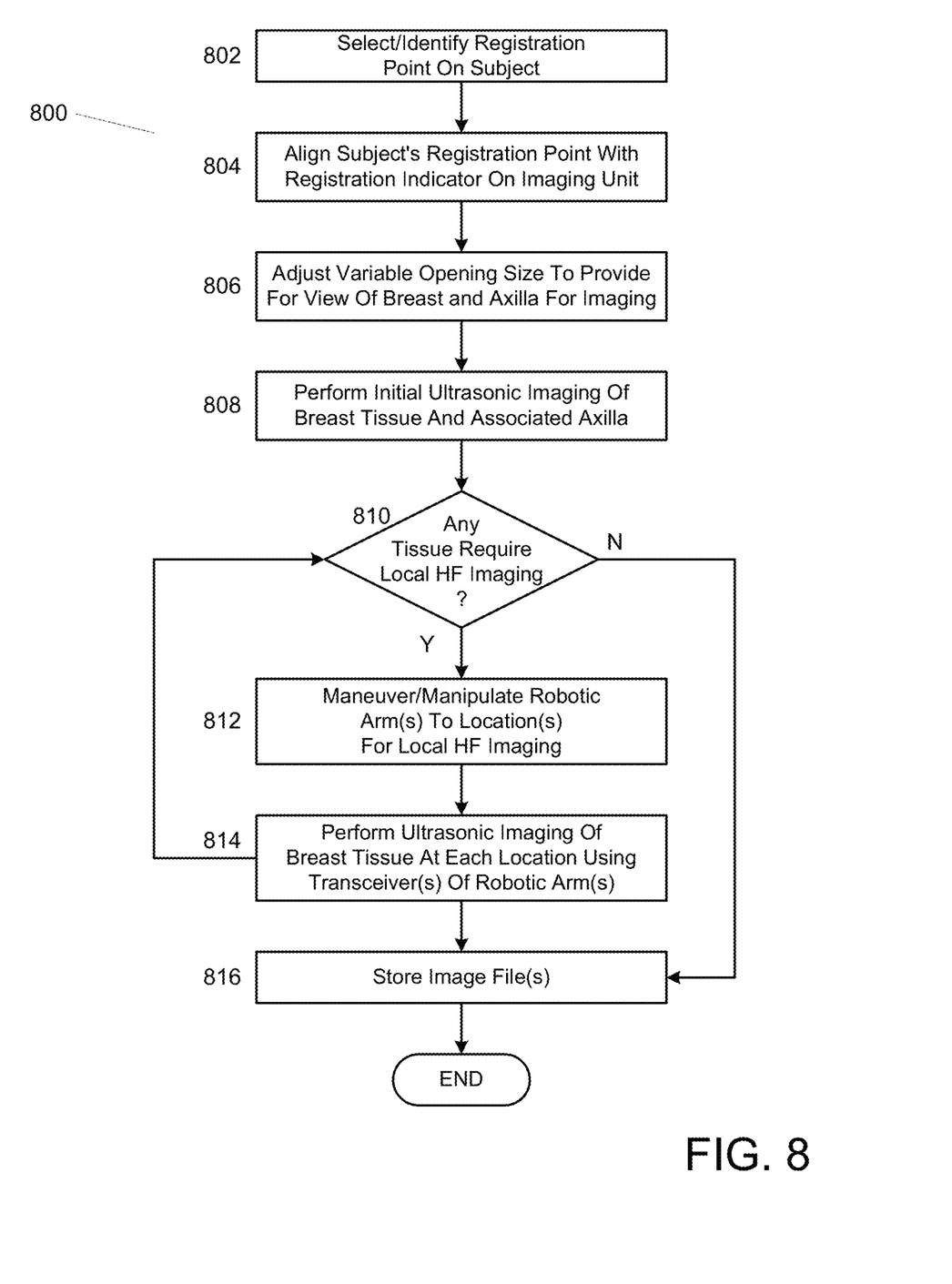
FIG. 8 is a flowchart illustrating one example of a sonographic imaging process that can be performed using implementations employing the teachings herein.
Figure 9:
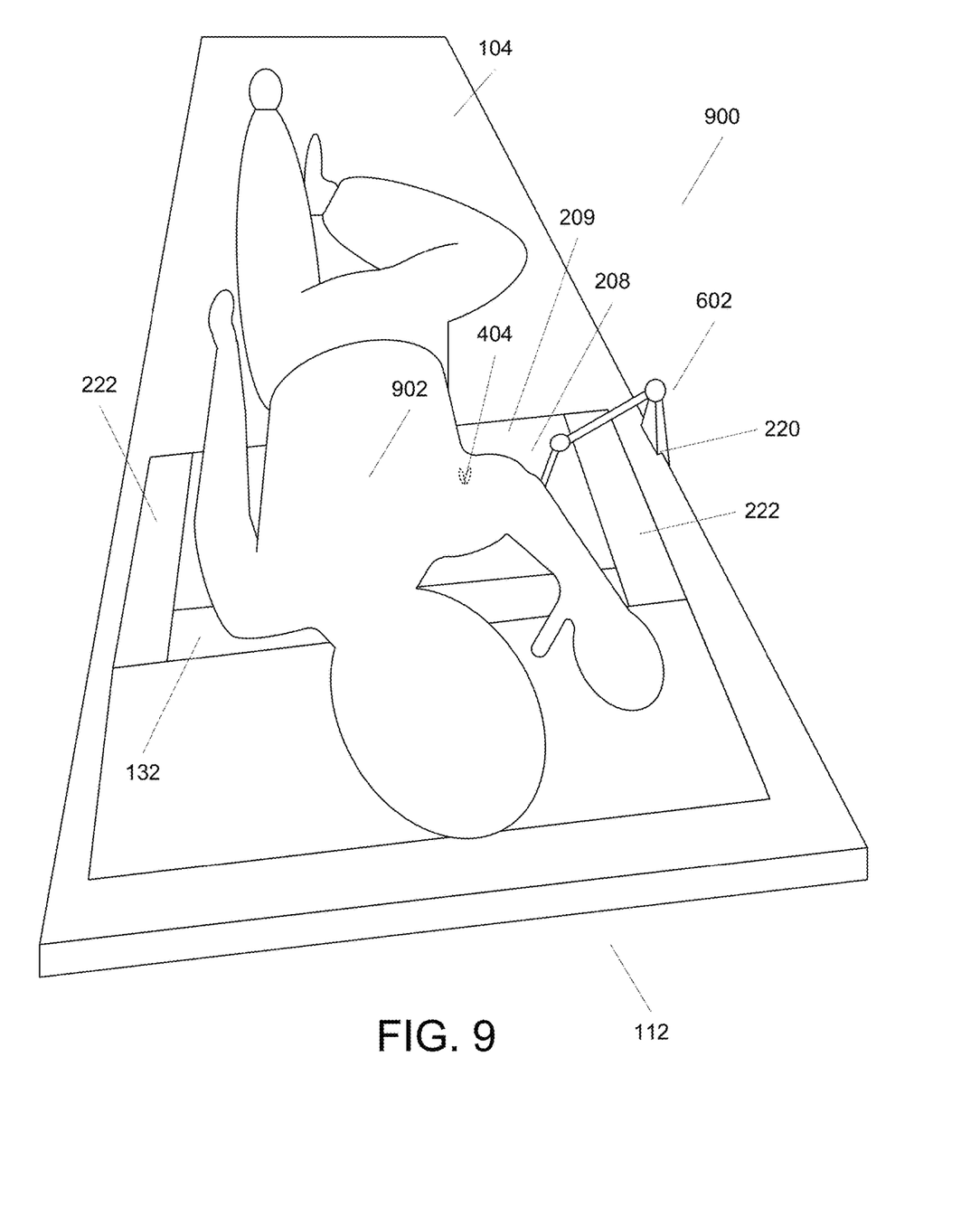
FIG. 9 illustrates, in simplified form, part of an example sonographic imaging unit constructed according to teachings based upon one or more of the examples described herein, with a simplified representation of a human subject positioned thereon in the prone position.

Now, the description will continue with reference to FIGS. 8-9, in which FIG. 8 is a flowchart 800 illustrating one example of a sonographic imaging process that can be performed using implementations employing the teachings herein, and to the drawing of FIG. 9, which illustrates, in simplified form, part 900 of an example sonographic imaging unit 112 constructed according to one or more of the examples described herein, with a simplified representation of a human subject 902 positioned thereon in the prone position. As shown, the example sonographic imaging unit 112 includes a robotic arm of one of the types described herein that is mounted to the exterior of the imaging unit 112, which was either a robotic arm 406 that was part of the imaging unit 112 as constructed or was a retrofit robotic arm 602 that was either added to an imaging unit 112 constructed as described herein or retrofit to a conventional sonographic imaging system. More particularly, as shown, the robotic arm 602 is one added to an imaging unit 112 constructed as described herein that is attached at a mounting point 220 external to the tub 208 and the part with the transducer 408 (not shown) extends down into the tub 208 via the opening 209.

The process begins with the selection/identification of a registration point in the human subject (Step 802). The registration point is a spot on the subject that is ideally selected in vertical alignment with the subject's nipple and between 1 cm and 4 cm below the inframammary fold. Note here that extreme precision is not a requirement, advantageously due to the mobility of the robotic arms. The goal however, is to ultimately have the breast positioned so that it is reasonably centered over the ultrasound transducer array unit 310 of FIG. 3 and the axillary lymph node(s) associated with the breast to be imaged is also positioned over the opening 209.

Depending upon the particular implementation, the selection/identification of a registration point can be performed by a nurse, aide or imaging technician, or, advantageously, it can be performed by the subject themselves. Moreover, in some approaches, a "sticker" having a biocompatible removable adhesive can be used to mark the registration point on the subject so that they can position themselves by matching the registration point with the registration indicator 206. In some further approaches, the registration point marker can be elevated and the registration indicator 206 can be slightly recessed, so that subject positioning can be tactile and ensured in a more positive manner. With still other implementations, the registration indicator 206 can be translucent or transparent and the registration point marker can be of a type that can be viewed with one of the cameras 126 through the registration indicator 206 to determine when the subject is properly positioned. Whatever approach is used, the registration point of the prone subject is aligned with the registration indicator 206 on the imaging unit 112 (Step 804 & FIG. 9).

The size of the variable opening 209 is adjusted as necessary by moving the sliding panel 132 (and if present and necessary the side panels 222) to ensure sufficient access for imaging the entire breast and the associated axillary lymph nodes 904 (Step 806). Depending upon the particular situation and subject, this step may be optional (e.g., if the then-current adjustment setting of the panel(s) 132, 222 is sufficient) or it may be performed before the subject is positioned in Step 802 (e.g., if the proper size opening is known prior to positioning). Still further, a combinational approach can also optionally be used, where the size of the variable opening 209 is preliminarily adjusted to close to what is required and then, once the subject 902 is properly positioned, the variable opening 209 size can be fine tuned.

Once the foregoing is complete and the subject 902 is positioned, initial low frequency ultrasonic imaging is performed (Step 808). Depending upon the particular implementation, this can be performed using the ultrasound transducer array unit 310 (if present) in a conventional manner, or it can be performed using the transducer(s) 408 of the robotic arm(s) 406, 602 according to, for example, pre-specified programming effected using the motion control circuitry 612, 712, or it can be performed using a combination of pre-specified programming and machine vision.

In addition, optionally, for ultrasound transducer array units that incorporate transducers that enable sonography at more than one frequency, this step may include taking multiple low frequency scans at different frequencies within the low frequency range.

Following the imaging of Step 808, one or more image(s) resulting from the scans can be reviewed on the display screen 116 at the operator console 114 to determine whether there are any areas of calcification, cysts, lesions or other abnormalities of actual or potential concern that should be the subject of local high frequency (HF) imaging (Step 810).

If any such areas of calcification, cysts, lesions or other abnormalities of actual or potential concern are identified, then more localized, and thorough imaging can be performed using the robotic arm(s) 406, 602. This is accomplished by maneuvering and manipulating the robotic arm(s) into positions near and/or about the locations of interest and using the transducers of the robotic arm(s) 406, perform HF ultrasound scanning of the localized area within the breast and/or axillary lymph nodes (Step 812). Then HF scanning can be conducted for each of the location(s) (Step 814) by cycling through Step 810 through Step 814 until all location(s) for which further imaging is desired has been completed. This HF scanning may involve obtaining reflective scans from different positions, or, where there are at least two robotic arms 406 or and ultrasound receiver array 504 is present, through proper orientation of the robotic arm(s) 406, through-transmission imaging can be performed. Again, depending upon the particular implementation, the HF imaging may involve use of machine vision and/or actions of someone at the operator console 114 to orient/re-orient the transducer(s) 408 of the robotic arms 406.

Once all of the relevant locations have been imaged, or if there is no tissue requiring local imaging (Step 810—"N") the resulting data/images are stored in one or more files (Step 816) for review by the relevant radiologist and/or other medical professional.

At this point, it should be noted that the foregoing process is applicable to one breast and its associated axillary lymph nodes. If imaging of the other breast and/or associated axillary lymph nodes is desired, the same process can be used on the other side. Alternatively, the selection/identification of the registration point (Step 802) for both sides can be performed at the same time, and then, once imaging of one side is complete, the subject merely would then shift their body to align the other side registration point with the registration indicator 206 (Step 804) and the process would continue as described above. Likewise, if the variable opening 209 and tub 208 are large enough, and the robotic arms have enough range, both breasts can potentially be positioned and imaged without repositioning of the subject.

Finally, it should be noted and understood that, while the above has been described with reference to imaging of human breast tissue and associated axillary lymph nodes, systems employing the teachings herein can be constructed for imaging other human body parts that are placed within a fluid-filled tub using one or more robotic arms having associated ultrasonic transducer(s) located thereon, where the ultrasonic transducer(s) are within the tub as well.

Advantages

As should be appreciated from the foregoing, different implementations of the above can provide one or more of the following advantages, and in many cases, provide several to many of the following advantages.

Through use of the variable opening, complete imaging of the full extent of the entire breast and axillary lymph nodes across 99+% of all body types (i.e., height, weight, breast size and shape, etc.) can be performed.

Through use of the robotic arm(s) complete imaging of the full extent of the entire breast in planes extending from the nipple to the chest wall can be performed.

Through use of the robotic arm(s) imaging of specific tissue can be performed from multiple directions and vantage points.

The presence of two or more robotic arm(s) makes both reflected and through transmission imaging from multiple vantage points possible.

Imaging using the robotic arms make it possible to more easily identify the type of lesion, if any, is present at a specific location.

The use of HF transceivers on the robotic arm(s) allows for the obtaining of sharper, more detailed images of specific tissue of interest and, greater ease in differentiating benign calcifications from cancerous tissue calcifications.

Likewise, use of HF transceivers on the robotic arm(s) allows for more accurate location and measurement of specific tissue of interest.

In the case of breast imaging, imaging of the axillary lymph nodes can be conducted, which are the first locations to which breast cancer will metastasize. Moreover, that imaging can be as part of the same procedure as the breast imaging, typically without even the need for the patient to be repositioned.

No constraining (e.g., by having the breast within a cone, sleeve or between plates) or tethering of breast tissue is required, so that images obtained using the teachings herein are not distorted by such constraint or tethering and thereby will closely correspond to images obtained via mammography, facilitating direct comparison between them.

Since no constraining or tethering is required, the lack of distortion allows for the acquired data to be used to accurately reproduce 3D models using that data.

Finally, since the subject is able to identify a registration point on themselves and align it with the registration indicator on the imaging unit, and the opening size and movement of the robotic arms can be remotely controlled, there is no need for the technician, operator, nurse or doctor/radiologist to touch or even go near the subject, enabling the imaging to occur with complete social distancing.

Having described and illustrated the principles of this application by reference to one or more examples, it should be apparent that embodiment(s) may be constructed and/or modified in arrangement and detail without departing from the principles disclosed herein and that it is intended that the application be construed as including all such modifications and variations insofar as they come within the spirit and scope of the subject matter disclosed.

The foregoing outlines, generally, the features and technical advantages of one or more implementations that can be constructed based upon the teachings in this disclosure in order that the following detailed description may be better understood. However, the advantages and features described herein are only a few of the many advantages and features available from representative examples of possible variant implementations and are presented only to assist in understanding. It should be understood that they are not to be considered limitations on the invention as defined by the appended claims, or limitations on equivalents to the claims. For instance, some of the advantages or aspects of different variants are mutually contradictory, in that they cannot be simultaneously present in a single embodiment. Similarly, some features or advantages may be applicable to one aspect and inapplicable to others. Thus, the foregoing features and advantages should not be considered dispositive in determining equivalence. Additional features and advantages will be apparent from the teachings of the description, drawings, and claims.

What is claimed is:

1. A sonographic imaging device comprising:
   a sonographic imaging unit including
   an upper surface having an opening therein;
   at least one movable panel, coupled to the upper surface, wherein sliding movement of the panel in a plane parallel to the upper surface will alter the overall size of the opening;
   a tub positioned beneath the opening and defining a volume for holding water such that, in use, a breast of a human subject can freely protrude through the opening into the water within the volume defined by the tub;
   at least two independently controllable robotic arms, each having a base, a terminal end and more than 3 degrees of freedom, wherein the base is coupled to a surface within the tub and wherein the terminal end of each is position-able to any of multiple angles at multiple locations within the volume for holding water defined by the tub to allow for positioning of the terminal end of at least one of the independently controllable robotic arms to a first location for imaging of the human subject's axillary lymph nodes associated with the breast as well as a second location for imaging the breast; and
   at least one high frequency ultrasound transducer located near the terminal end of the at least two independently controllable robotic arms.

2. The sonographic imaging device of claim 1, further comprising:
   at least one camera located within the tub.

3. The sonographic imaging device of claim 2, wherein the at least two robotic arms comprise more than two robotic arms.

4. The sonographic imaging device of claim 1, wherein the at least two robotic arms comprises at least one snake-type robotic arm and including more than five individually articulable links between the base and the terminal end thereof.

5. The sonographic imaging device of claim 1, wherein the at least one movable panel comprises a sliding panel that varies a height of the opening.

6. The sonographic imaging device of claim 1, wherein the at least one movable panel comprises a panel that varies a side dimension of the opening.

7. The sonographic imaging device of claim 1, further comprising:
   a low frequency ultrasound transducer array unit within the tub.

8. The sonographic imaging device of claim 1, further comprising:
   an ultrasound receiver array within the tub.

9. The sonographic imaging device of claim 1, wherein:
a first transceiver of a first of the at least two robotic arms, when operating, will be a transmitter of ultrasound radiation, and
a second transceiver of a second of the at least two robotic arms, when operating, will be a receiver of at least some of the ultrasound radiation transmitted by the first transceiver.

10. A method of acquiring sonographic images of unconstrained breast tissue of a human subject positioned on a surface of an imaging unit, when at least the breast's internal tissue is present within fluid within a volume of a tub, the method comprising:
i) adjusting a size of an opening, defined by the surface of the imaging unit, by sliding a movable panel in a plane parallel to the surface in order to accommodate a portion of the human subject containing the internal breast tissue and allow for imaging of the axillary lymph nodes associated with the human subject's breast;
ii) conducting a low frequency ultrasound imaging scan of the internal breast tissue, from a vantage point at a first position within the tub, using a low frequency ultrasound transducer array unit present within the fluid within the tub;
iii) from sonographic data obtained via the low frequency ultrasound imaging scan, identifying specific tissue of the internal tissue that is to be subjected to local high frequency ultrasound imaging;
iv) maneuvering within the fluid within the volume, in a concurrent combination of X, Y and Z directions, a distal terminal end of at least one robotic arm of at least two independently controllable robotic arms, each having a base and independently having more than 3 degrees of freedom, the at least one robotic arm having a high frequency transceiver near the distal terminal end thereof, within the tub to a new position that is closer to the specific tissue and suitable for conducting local high frequency ultrasound imaging of the specific tissue from a first vantage point different from the vantage point of the low frequency ultrasound transducer array unit, wherein the base of the at least one robotic arm is within, and coupled to a surface of, the tub;
v) obtaining sonographic data, using the high frequency transceiver, from which at least one image of the specific tissue from the vantage point can be generated;
vi) in conjunction with at least one of "ii)" or "v)", imaging the axillary lymph nodes associated with the internal breast tissue being imaged, and vii) storing the sonographic data resulting from at least the high frequency imaging in non-transitory storage.

11. The method of claim 10 wherein the maneuvering further comprises:
positioning the high frequency transceiver based upon a view from at least one camera within the tub.

12. The method of claim 10 further comprising:
using machine vision in conjunction with the at least one camera to perform at least some of the positioning.

13. The method of claim 10 further comprising:
modifying a position of at least one independently movable side panel coupled to the surface of the imaging unit through sliding movement, relative to the surface of the imaging unit, in a plane that is parallel to the surface of the imaging unit so as to change a width of the opening.

14. The method of claim 10, further comprising:
maneuvering the at least one robotic arm from the position to a new position suitable for conducting local high frequency imaging of the specific tissue from a new vantage point different from the first vantage point and the vantage point of the low frequency ultrasound transducer array unit.

15. The method of claim 10, wherein the at least one robotic arm includes a first robotic arm having a first transceiver which, when operating, will act as an ultrasound transmitter, and a second robotic arm having a second transceiver which, when operating will act as an ultrasound receiver, and wherein the method further comprises:
positioning the first transceiver at a first position on one side of the specific tissue and positioning the second transceiver on a side of the specific tissue opposite the one side such that no plane defined by the first and second transceivers are parallel to the surface and, during imaging in a first direction, at least some ultrasound radiation will pass from the first transceiver through the specific tissue to the second transceiver; and
obtaining through-transmission sonographic data for the first position using the first transceiver and second transceiver as the sonographic data.

16. The method of claim 15, wherein the through-transmission sonographic data is first through-transmission sonographic data and wherein the method further comprises:
repositioning the first transceiver to a new position relative to the specific tissue different from the first position and positioning the second transceiver opposite the new position such that the specific tissue is between the first transceiver and second transceiver defining a new direction for imaging such that, during imaging in the new direction, at least some ultrasound radiation will pass from the first transceiver through the specific tissue to the second transceiver; and
obtaining through-transmission sonographic data for the new position using the first transceiver and second transceiver.

17. The method of claim 16, wherein the repositioning includes:
using at least one camera within the tub to maneuver the first transceiver from the first position to the new position.

18. The method of claim 10, further comprising:
aligning a registration point on the human subject with a registration indicator on an upper surface of the imaging unit.

19. The method of claim 10, wherein the adjusting the size of the opening is performed, while the human subject is lying in a prone position on the surface of the imaging unit, based upon a view from at least one camera within the tub.

20. The method of claim 10, wherein the adjusting the size of the opening is performed such that at least an area extending from, in a first direction, the clavicle of the human subject to at least 1 cm below the inframammary fold of the human subject and, in a second direction, from a tricep-side of the axillary lymph nodes associated with the breast to the sternum-side of the breast where skin of the breast meets the chest wall.

21. The method of claim 20, further comprising:
imaging the axillary lymph nodes associated with the human subject's breast using at least one of the low frequency ultrasound transducer array unit or the high frequency transceiver.

* * * * *

UNITED STATES PATENT AND TRADEMARK OFFICE
CERTIFICATE OF CORRECTION

| | | |
|---|---|---|
| PATENT NO. | : 11,324,480 B1 | Page 1 of 1 |
| APPLICATION NO. | : 17/221466 | |
| DATED | : May 10, 2022 | |
| INVENTOR(S) | : Philip B. Kivitz | |

It is certified that error appears in the above-identified patent and that said Letters Patent is hereby corrected as shown below:

In the Claims

In Column 13, Line 57, in Claim 12, delete "claim 10" and insert -- claim 11 -- therefor.

Signed and Sealed this
Twentieth Day of June, 2023

Katherine Kelly Vidal
*Director of the United States Patent and Trademark Office*